United States Patent
Mukherjee et al.

(10) Patent No.: US 6,187,827 B1
(45) Date of Patent: Feb. 13, 2001

(54) PROCESS FOR THE RECOVERY OF METHYL POLYSILOXANES IN THE FORM OF CYCLOSILOXANES

(75) Inventors: Soumitra Ranjan Mukherjee, 15 NB, Block - A, 2$^{nd}$ Floor, New Alipore, Calcutta 700 008 (IN); Amit Kumar Paul, Calcutta (IN)

(73) Assignee: Soumitra Ranjan Mukherjee (IN)

( * ) Notice: Under 35 U.S.C. 154(b), the term of this patent shall be extended for 0 days.

(21) Appl. No.: 09/254,669

(22) PCT Filed: Sep. 12, 1997

(86) PCT No.: PCT/AU97/00601

§ 371 Date: Mar. 12, 1999

§ 102(e) Date: Mar. 12, 1999

(87) PCT Pub. No.: WO98/11155

PCT Pub. Date: Mar. 19, 1998

(30) Foreign Application Priority Data

Sep. 13, 1996 (AU) .................................. 65599/96

(51) Int. Cl.$^7$ .................................. C08J 11/24
(52) U.S. Cl. .................... 521/47.5; 556/460; 528/489; 528/499; 528/495; 528/501; 528/487
(58) Field of Search .................... 521/47.5; 556/460; 528/489, 499, 495, 501, 487

(56) References Cited

U.S. PATENT DOCUMENTS 5,110,972 * 5/1992 Greenlee .

* cited by examiner

Primary Examiner—Robert Dawson
Assistant Examiner—Kuo-Liang Peng
(74) Attorney, Agent, or Firm—Pendorf & Cutliff

(57) ABSTRACT

A process for the recovery of methyl polysiloxane in the form of methyl cyclosiloxane of the general formula $(R_2SiO)_x$, wherein R is selected from alkyl, alkenyl, aryl and alkaryl groups and "x" is an integer selected from 3–6, in which:

a) liquifying silicone feedstock as herein defined is liquefied in a solvent selected from alcohol or siloxane in presence of a catalyst at a temperature of between 110° C.–180° C. to obtain a liquefied mass consisting of a mixture of methyl polysiloxane, solvent and filler;

b) adding a metal hydroxide to the liquefied mass so as to convent the fillers to their corresponding silicates, the said silicates thus obtained are removed and the liquid recovered; and c) cyclyzing methyl polysiloxane in the liquid medium thus obtained in the presence of a cracking catalyst in the temperature range of 115–160° C. so as to crack the liquid methyl polysiloxane to a mixture of volatile methyl cyclosiloxane.

The process may be used to recover methyl cyclosiloxane from silicone containing scrap material.

10 Claims, No Drawings

PROCESS FOR THE RECOVERY OF METHYL POLYSILOXANES IN THE FORM OF CYCLOSILOXANES

BACKGROUND OF THE INVENTION

1. Field of the Invention

The present invention relates to a process for the recovery of methyl cyclosiloxane from silicone scrap material, which includes elastomeric scrap, parings, mold flashes, mold component, extruded profile, RTV mold and off-specification discarded material of silicone polymers hereinafter referred to as 'silicone feedstock'. More particularly the present invention relates to a process in which almost pure cyclics are recovered from silicone feedstock without generating further secondary waste. Methyl cyclosiloxanes is used in the manufacture of silicone polymers.

The silicone feedstock that is available can be in different forms e.g., cured, partially cured or uncured silicone in the form of heat cured rubber (HCR); room temperature vulcanising, (both RTV-1 & RTV-2) and liquid silicone rubber (LSR). They may be condensation or addition cured type, filled with reinforcing and/or semi-reinforcing fillers, having no or little commercial utility in their commonly available form or quality.

The difficulty faced by the industry was to recover Methyl cyclosiloxane from filler filled silicone feedstock. Almost all such silicone feedstock contain fumed silica, also known as silicic acid, colloidal silica, millimicron silica etc., as reinforcing fillers. No process is known for recovering cyclics from such filler filled silicone feedstock successfully. In case of filled silicone feedstock, with mainly fumed silica, corresponding metal silicates are produced. Metal silicates find multifarious use in industrial process and can be disposed of.

First the silicone feedstock is liquified in presence of anionic surfactants/amines and/or mineral acids as catalyst where a volatile solvent is used as media. When fumed silica is present in the silicone feedstock, it is removed as a silicate from the liquid mixture by decantation or mechanical separation. After separation of such filler, the volatile solvent is removed by stripping at low pressure and Methyl polysiloxane is obtained as a residue. Methyl polysiloxane can be converted to a mixture of cyclics by cracking with alkali metal hydroxide or mineral acid at high yields which is as high as over 90%.

2. Desription of the Related Art

The use of silicone and silicone containing materials are increasing world-wide and a significant quantity of such silicone feedstock are generated during manufacture and processing of such silicone products. The known process for the utilization of silicone feedstock lacks versatility and is applicable to a particular type of silicone feedstock. In some cases, recovery was very low.

U.S. Pat. No. 4,111,973 issued to Bluestein relates to an improved process for obtaining better yield and purity of fluoroalkyl cyclotrisiloxane in a cracking reaction of diorgano polysiloxane using an effective amount of aliphatic alcohol as a stabilising agent with addition an effective amount of cracking catalyst.

This process is specifically directed to the recovery of pure fluoroalkyl cyclosiloxane from a mixture of diorganopolysiloxanes. The text of this patent is silent as to the effects on the gel mass when small amount of trifunctional groups, is present as impurity. Therefore, this process is only applicable to pure difunctional alkyl polysiloxane.

U.S. Pat. No. 4,764,631 issued to Halm et al provides a method for preparing a product cyclodiorganopolysiloxalle via the vapour phase re-arrangement of other cyclopolydiorganosiloxane or mixtures thereof. This process is also applies to pure difunctional cyclopolydiorganosiloxane and the process is applicable to silicone feedstock which are in the form of volatile cyclics only.

U.S. Pat. No. 2,860,152 issued to Fletcher teaches a method of producing cyclic diorganosiloxanes having a composition different from starting organo polysiloxane. In this process the diorgano polysiloxane and an inert solvent having b.p. more than 250° C. were used. At least 20% by wt. of the siloxane was used as solvent. Temperature and pressure in reaction zone were maintained in a manner such that in presence of alkali catalyst, only cyclics were available from the reaction mixture while the solvent remained non-volatile under those conditions. The inert solvent shifts the polymer/cyclic equilibrium of the reaction more towards the cyclics and with more cyclics in the reactor, lesser the tendency of the reaction mass to gel. Therefore, at least 20% solvent is required to delay the gelation of the reaction mass. However, at the end of run, when the reaction mass gets gelled, the entire reaction mass is discharged as the siloxane/solvent cannot be separated.

Thus, the process does not completely resolve the problem of gelation and therefore recovery is poor.

U.S. Pat. No. 5,420,325 issued to John S Razzano teaches a method of producing cyclics where an effective amount of high boiling alcohol is used in the liquid siloxane hydrolysate. The high boiling alcohol allows the removal of trifunctional species in an efficient manner and completely eliminates formation of a gel. The siloxanes and the alcohol in the residue can be recovered and reused. Thus, Razzano has resolved the problem of gelation by cracking a diorganopolysiloxane containing a portion of trifunctional group to a mixed cyclosiloxane. Razzano has not, however, taught as to how to recover the remaining siloxane from alcohol.

In the aforesaid literature the focus has been on the cracking of a liquid organopolysiloxane containing a portion of trifunctional group but there is no teaching with regard to silicone feedstock filled with fillers, specially fumed silica. These processes can function only in case of liquid methyl polysiloxane which is free of fillers.

U.S. Pat. No. 5,110,972 issued to Tremco Incorporated teaches a method where silicone scrap is dissolved in high boiling solvent (b.p. greater than cyclics) and sulphuric acid. The sulphuric acid is then neutralized with KOH and with additional of KOH methyl polysiloxane is cracked to cyclics at 115° C. under reduced pressure. Again, the said process can only be applied to unfilled feedstock.

There is no teaching in this prior art as to how the residual silicone is separated from filler and solvent rich residue. Thus this process also does not aim at solving the problem of recovery of methyl polysiloxane from filler filled scrap.

Chinese Patent No. CN 1086518A describes a method of manufacturing organocyclic silicone compounds by pyrolysis of silicone rubber under atmospheric pressure. This patent uses silicone rubber as a raw material. After washing and breaking into small pieces, the rubber is mixed with organo cyclosiloxane compounds and reacted in presence of KOH as a catalyst under normal atmospheric pressure and at 200–500° C. This process produces unfavourable results at 200–500° C. in presence of KOH because demethylation of dimethylpolysiloxane occurs rapidly, leading to an explosion.

German Patent No. DE 4126319 A1 relates to a process for the recovery of silicone cyclic from silicone rubber. In this invention, silicone rubber is pyrolyzed at 550–600° C. under vacuum and/or inert atmosphere. Major component in the outlet is Hexamethylcyclotrisiloxane (D3). In this paper the process and apparatus used are not clear. Even if practicable, the capital cost of such process using rotating pipe oven will be extremely high because of (a) nonfeasibility of high temperature rotary seal; (b) inert gas blanketing of seal face against accidental leak; (c) complex anti-fouling condensing of D3, a major condensate which sublimes at 64° C.; (d) hazardous in combination with oxygen at 600° C. as this causes rapid oxidation; (e) non-continuous operation due to intermittent cleaning of reactor walls of complex crust formed; (f) progress of pyrolysis hindered by crust formed around the rubber; (g) long retention time for complete pyrolysis. With these disadvantages this process has many practical drawbacks. None of the prior art therefore teaches recovery of siloxane from a non-specific silicone feedstock in such a way that process will be free from waste generation and will be environment friendly.

SUMMARY OF THE INVENTION

It is an object of the present invention to provide a process for the recovery of methylcyclosiloxane from silicone feedstock where the effluent is environment friendly and free from pollutants.

It is a further object of the present invention to provide any efficient and economical process for the recovery of methyl cyclosiloxanes from fumed silica filled silicone feedstock.

DETAILED DESCRIPTION OF THE INVENTION

Accordingly, the present invention relates to a process for producing a mixture of methyl cyclosiloxanes of general formula $(R_2SiO)_x$, where R is selected from alkyl, alkenyl, aryl and alkaryl groups and "x" is an integer selected from 3–6.

According to the present invention there is provided a process for the recovery of methyl polysiloxane in the form of methyl cyclosiloxane of the general formula, $(R_2SiO)_x$ wherein R is selected from alkyl, alkenyl, aryl and alkaryl groups and "x" is an integer selected from 3–6, in which:

a) liquifying silicone feedstock as herein defined is liquefied in a solvent selected from alcohol or siloxane in presence of a catalyst at a temperature of between 110° C.–180° C. to obtain a liquified mass consisting of a mixture of methyl polysiloxane, solvent and filler;

b) adding a metal hydroxide to the liquified mass so as to convert the silica fillers to their corresponding silicates, the said silicates thus obtained are removed and the liquid recovered; and c) cyclyzing methyl polysiloxane in the liquid medium thus obtained in the presence of a cracking catalyst in the temperature range of 115to 160° C. so as to crack the liquid methyl olysiloxane to a mixture of volatile methyl cyclosiloxane.

When the solvent used in the process is a non-silicone compound the process further comprises stripping the liquid resulting from step (b) to separate the solvent from the mixture.

The starting material employed in the process of the invention is silicone feedstock. Silicone feedstock contains organosiloxane polymers in which the substituting groups are methyl, phenyl, vinyl and/or other hydrocarbon radicals. Such polymers may or may not contain inorganic fillers, silanes, organic additives and catalyst. Such silicone feedstock may be in the form of solid, semi-solid, paste, gel and thixotropic compounds.

A: Liquification

In this step solvent is added to the silicone feedstock. The solvent is selected from alcohol from $C_5$ to $C_{12}$ and/or silicone cyclics. Most preferred solvent is Octyl alcohol, 2-Ethyl Hexanol and/or mixed methyl cyclosiloxane. In the liquification of filler filled silicone waste, an anionic surfactant is used as catalyst for linearization. Mineral acids/ tertiary amines can also be used. Linear alkyl benzene sulphonic acid is the most preferred liquification catalyst. For liquification, a pressure vessel is used with an agitator. A temperature in the range of 110–180° C. is employed for liquification. The preferred temperature of liquification is about 140° C. Pressure in the range of 2 to 8 $Kg/cm^2$ is required to aid the liquification. The preferred pressure for liquification is about 4 $Kg/cm^2$ When tertiary amines are used in the step of liquification the amines come out of the reaction mass as an unreacted (ready for reuse) immiscible layer in-between the siloxane and silicate. After completion of the reaction the metal silicates may be removed from the reaction mass in a known manner.

B. Separation of Filler

In the step of separation the silica fillers containing free OH groups are reacted with metal hydroxide and separated out as metal silicates. The removal is effected by converting the fumed silica in the fillers to Na-silicate, Ca-Silicate and Al-Silicate or mixture thereof, by the use of their corresponding hydroxides. In the step of separation an effective amount of $Ca(OH)$, $NaOH$ or $Al(OH)_3$ or mixture thereof is added to the liquified mixture with a small amount of water for formation of the corresponding silicates. A temperature in the range of 110 to 220° C. is required for the separation. The pressured temperature is about 170° C. The pressure of 2 to 10 $Kg/cm^2$ and preferably about 4 $Kg/cm^2$ is used.

C. Separation of Solvent

After separation of fillers, the liquid contains a mixture of liquid methyl polysiloxane and solvent. The step of separation of solvent is optional. The step of separation of solvent is not required when silicone cyclics are use as solvent. When the solvent is separated it is effected by stripping under heat and reduced pressure. Recovered solvent is recycled to the liquification stage.

D. Cyclization of Linear Methyl Polysiloxane

The liquid methyl polysiloxane after removal of filler and solvent (if necessary) is cracked to a mixture of volatile methyl cyclosiloxanes in presence of an alkali metal hydroxide or other known catalyst (mineral acids, etc.). Potassium hydroxide is used as catalyst for cracking the liquid methyl polysiloxane. A temperature in the range of 115°–160° C. is needed for cracking of under reduced pressure. The optimum temperature for cyclization is 140° C. under reduced pressure. The process is continuous, but only a small amount of water is required to be charged at regular intervals for cyclic formation. Initially, a 50% water solution of KOH is used. Cracked cyclics are found to essentially contain a mixture of one or more of Hexamethylcyclotrisiloxane (D3), Octamethylcyclotetrasiloxane (D4), Decanethylcyclopentasiloxane (D5), and Dodecamethylcyclohexasiloxane (D6).

EXAMPLES

Example 1

Step 1:—1500 gm of Octyl alcohol was added to a 5 litre capacity SS pressure withstanding reactor with an agitator. 15 gm of Linear Alkyl Benzene Sulphonic acid(LABS) was added under stirring. After mixing of LABS, pieces of cured HCR rubber (a grade having Shore-A-Hardness of 40 and primarily loaded with fumed silica) was charged into the reactor as the feedstock and heated to 140° C. At 140° C. the pressure was set to 4 $Kg/cm^2$. Reaction was carried out for 4 hrs. The whole mass in the reactor became liquid after 4 hrs. of reaction.

Step 2:—750 gm. of 50% aqueous NaOH was added to reaction mass and heated to 140° C. and pressure adjusted to 4 $kg/cm^2$. Reaction was carried out for 1 hr. and thereafter cooled and 1125 gms of Sodium Silicate was separated.

Step 3:—Octyl alcohol was stripped out form the neutralized liquid mixture in the reactor, under 750 mm Hg vacuum at 130° C. 1480 gm of Octyl alcohol was obtained.

Step 4:—The residue present in reactor, after alcohol stripping, was cracked with 20 gm of 50% aqueous KOH solution at 140° C. 1030 gm. of cyclics was obtained.

Examples 2, 3 & 4

Example 1 was repeated using different amount of the ingredients shown in Examples 2, 3 and 4 in Table 1. Composition of Cyclics is given in Table 2.

TABLE 1

| Example: | 1 | 2 | 3 | 4 |
|---|---|---|---|---|
| Type of rubber (feedstock) | HCR | RTV-1 | RTV-1 | RTV-1 |
| Type of Crosslinker | peroxide | oxime | Acetoxy | Alcoxy |
| Marketed By | Wacker-FG | Wacker-USA | GE-India | GE-India |
| Grade | R-415140 | T-192 | Winsil 10 | Winsil 20 |
| Inputs | In Gms; | | | |
| Rubber (feedstock) | 1500 | 1500 | 1500 | 1500 |
| Octyl alcohol | 1500 | 1500 | 1500 | 1500 |
| LAB Sulphonic Acid | 15 | 80 | 15 | 15 |
| 50% Aq. NaOH | 750 | 375 | 375 | 375 |
| Outputs | | | | |
| Sodium Silicate | 1125 | 510 | 517 | 380 |
| Octyl Alcohol | 1480 | 1475 | 1485 | 1485 |
| Cyclics | 1030 | 1285 | 1270 | 1255 |

TABLE 2

| Example No: | 1 | 2 | 3 | 4 |
|---|---|---|---|---|
| Theoretical Siloxane* .gm (i.e. di tri & tetra functional) | 1125 | 1320 | 1335 | 1335 |
| Volatiles obtained, gm. | 1030 | 1285 | 1270 | 1255 |
| % of Siloxane recovered | 90.25 | 94.61 | 92.48 | 90.98 |
| Composition of Cyclics (% by GC) | | | | |
| Water | 0.92 | 1.19 | 1.09 | 1.29 |
| D3 | 15.10 | 6.53 | 7.82 | 6.57 |
| D4 | 62.04 | 72.13 | 70.94 | 70.08 |
| D5 | 18.98 | 16.90 | 16.28 | 18.27 |
| D6 | 2.46 | 1.63 | 2.18 | 1.88 |
| Others | 0.50 | 1.62 | 1.69 | 1.92 |

Examples 5, 6, 7 & 8

The process of the Example 1 was repeated with variation in amounts and ingredient and conditions as mentioned here. Here $Al(OH)_3$ was used instead of NaOH. Temperature and pressure required to form Aluminium Silicate were 170° C. and 4 kg/cm². Reaction time was 6 hrs. Inputs and outputs are shown in Table 3. Composition of Cyclics are shown in Table 4. Here the separated silicate was removed as solid residue.

TABLE 3

| Example: | 5 | 6 | 7 | 8 |
|---|---|---|---|---|
| Type of rubber (feedstock) | HCR | RTV-1 | RTV-1 | RTV-1 |
| Type of Crosslinker | peroxide | oxime | Acetoxy | Alcoxy |
| Marketed By | Wacker-FG | Wacker-USA | GE-India | GE-India |
| Grade | R-415/40 | T-192 | Winsil 10 | Winsil 20 |
| Inputs In Gms. | | | | |
| Rubber (feedstock) | 1500 | 1500 | 1500 | 1500 |
| Octyl alcohol | 1500 | 1500 | 1500 | 1500 |
| LAB Sulphonic Acid | 15 | 80 | 15 | 15 |
| Aluminum Hydroxide | 300 | 150 | 150 | 150 |
| Outputs | | | | |
| Aluminum Silicate | 600 | 300 | 309 | 305 |
| Octyl Alcohol | 1475 | 1470 | 1480 | 1485 |
| Cyclics | 1050 | 1275 | 1276 | 1264 |

TABLE 4

| Example No: | 5 | 6 | 7 | 8 |
|---|---|---|---|---|
| Theoretical Siloxane* .gm (i.e. di, tri & tetra functional) | 1125 | 1320 | 1335 | 1335 |
| Volatiles obtained, gm. | 1050 | 1275 | 1276 | 1264 |
| % of Siloxane Recovered | 91.49 | 95.19 | 93.68 | 93.52 |
| COD of Sludge, mgO$_2$/Kg Solid. | 30.30 | 38.70 | 39.10 | 29.33 |
| Composition of Cyclics (% by GC) | | | | |
| Water | 0.762 | 0.902 | 1.000 | 0.536 |
| D3 | 9.45 | 9.40 | 9.23 | 8.98 |
| D4 | 70.22 | 71.76 | 71.29 | 72.05 |
| D5 | 15.26 | 14.22 | 14.41 | 15.77 |
| D6 | 3.1 | 3.17 | 3.09 | 1.98 |
| Others | 1.208 | 0.548 | 0.980 | 0.684 |

In example 5 to 8, it was observed that solid Al-Silicate was formed which is inert and insoluble in water. In each case, the COD of the solid was below 40 mg O$_2$.Kg. Recovered solvent was 99% pure (by GC). The above reactions can be done similarly with Ca(OH)$_2$ or with other alkaline Metal hydroxide or mixture thereof.

Examples 9, 10, 11 & 12.

The process of Example 1 was used. Here mixed methyl cyclosiloxane was used instead of Octyl alcohol as a solvent. Temperature and Pressure required to form Sodium Silicate were 140° C. and 4 kg/cm$^2$. Reaction time was 2 hr. After separation of Sodium Silicate from the mixture, the residual liquid was cracked directly with KOH solution. Inputs and outputs are as below in table 5. Composition of Cyclics are in Table 6.

TABLE 5

| Example: | 9 | 10 | 11 | 12 |
|---|---|---|---|---|
| Type of rubber (feedstock) | HCR | RTV-1 | RTV-1 | RTV-1 |
| Type of Crosslinker | peroxide | oxime | Acetoxy | Alcoxy |
| Marketed By | Wacker-FG | Wacker-USA | GE-India | GE-India |
| Grade | R-415140 | T-192 | Winsil 10 | Winsil 20 |
| Inputs In Gms. | | | | |
| Rubber (feedstock) | 1500 | 1500 | 1500 | 1500 |
| Mixed methyl cyclosiloxane | 1500 | 1500 | 1500 | 1500 |
| LAB Sulphonic Acid | 30 | 160 | 30 | 30 |
| 50% Aq NaOH | 750 | 375 | 375 | 375 |
| Outputs | | | | |
| Sodium Silicate | 1125 | 510 | 517 | 380 |
| Cyclics | 2544 | 2789 | 2780 | 2766 |

TABLE 6

| Example No: | 9 | 10 | 11 | 12 |
|---|---|---|---|---|
| Theoretical Siloxane* .gm (i.e. di, tri & tetra functional) | 1125 | 1320 | 1335 | 1335 |
| Volatiles obtained, gm. | 1044 | 1289 | 1280 | 1266 |
| % of Siloxane Recovered | 92.34 | 97.46 | 94.22 | 94.54 |
| Composition of Cyclics (% by GC) | | | | |
| Water | 0.50 | 0.19 | 0.26 | 0.31 |
| D3 | 12.22 | 10.33 | 9.26 | 9.99 |
| D4 | 69.22 | 70.76 | 68.88 | 69.65 |
| D5 | 15.85 | 16.74 | 19.06 | 17.84 |

TABLE 6-continued

| Example No: | 9 | 10 | 11 | 12 |
|---|---|---|---|---|
| D6 | 2.23 | 1.98 | 2.54 | 2.21 |
| Others | Trace | Trace | Trace | Trace |

*The expression theoretical siloxane is not a standard terminology in the art. In the present invention. the rubber was dissolved in a non polar solvent and fillers were removed by sigh

We claim:

1. A process for the recovery of methyl polysiloxane in the form of methyl cyclosiloxane of the general formula, (R$_2$SiO)x wherein R is selected from alkyl, alkenyl, aryl or alkaryl groups and "x" is an integer selected from 3–6, comprising:
   a) liquifying silicone feedstock in a solvent selected from alcohol or siloxane in the presence of a catalyst at a temperature of between 110–180° C. to obtain a liquefied mass consisting of a mixture of methyl polysiloxane, solvent and filler;
   b) adding a metal hydroxide to the liquified mass so as to convert the silica fillers to their corresponding silicates, removing the said silicates thus obtained and recovering the liquid; and
   c) cyclyzing the methyl polysiloxane in the liquid medium thus obtained in the presence of a cracking catalyst in the temperature range of 115–160° C. so as to crack the liquid methyl polysiloxane to a mixture of volatile methyl cyclosiloxane.

2. A process as claimed in claim 1 wherein the solvent is alcohol having C$_5$ to C$_{12}$ carbon atoms.

3. A process as claimed in claim 2 wherein the alcohol is Octyl alcohol.

4. A process as claimed in claim 2, wherein the liquid recovered in step (b) is stripped to separate the solvent from the mixture.

5. A process as claimed in claim 1 wherein the siloxane is mixed methyl cyclosiloxane.

6. A process as claimed in claim 1, wherein the catalyst in step a) is selected from anionic surfactant, mineral acids and tertiary amines.

7. A process as claimed in claim 6, wherein the anionic surfactant is linear alkyl benzene sulphonic acid.

8. A process as claimed in claim 1, wherein the metal hydroxide is selected from Ca(OH)$_2$, NaOH and Al(OH)3.

9. A process as claimed in claim 1, wherein the cyclization is effected in the presence of a cracking catalyst preferably potassium hydroxide.

10. A process as claimed in claim 1 of wherein the methyl cyclosiloxane obtained comprises a mixture of one or more of Hexamethylcyclotrisiloxane, Octamethylcyclotetrasiloxane, Decamethylcyclopentasiloxane and Dodecamethylcyclohexasiloxane.

* * * * *